United States Patent [19]
Blade et al.

[11] Patent Number: 5,326,755
[45] Date of Patent: Jul. 5, 1994

[54] CERTAIN 2,4-PENTADIENAMIDE PESTACIDES

[75] Inventors: Robert J. Blade; George S. Cockerill, both of Hertfordshire, Great Britain

[73] Assignee: Roussel UCLAF

[21] Appl. No.: 923,970

[22] PCT Filed: Apr. 8, 1991

[86] PCT No.: PCT/GB91/00539
  § 371 Date: Sep. 10, 1992
  § 102(e) Date: Sep. 10, 1992

[87] PCT Pub. No.: WO91/16301
  PCT Pub. Date: Oct. 31, 1991

[30] Foreign Application Priority Data

Apr. 12, 1990 [GB] United Kingdom ................ 9008380

[51] Int. Cl.$^5$ .............. C07F 7/10; C07C 233/12; C07C 222/47; A01N 55/00
[52] U.S. Cl. ............................. 514/63; 514/524; 514/526; 514/549; 514/599; 556/465; 558/388; 558/390; 560/9; 560/19; 560/21; 560/41; 560/147; 560/153; 560/160; 560/163; 560/170; 564/162; 564/163; 564/182; 564/204
[58] Field of Search .............. 546/291; 564/182, 112, 564/163, 204; 514/346, 599, 615, 63, 524, 526, 549; 556/465; 558/388, 390; 560/9, 19, 21, 41, 147, 153, 160, 163, 170

[56] References Cited
PUBLICATIONS

Chemical Abstracts, vol. 117 (19) Abst. No. 117:19), 490–(b) Nov. 9, 1992.

*Primary Examiner*—Alan L. Rotman
*Attorney, Agent, or Firm*—Bierman and Muserlian

[57] ABSTRACT

The present application discloses pesticidally active compounds of formula I:

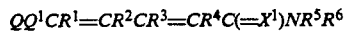

$$QQ^1CR^1=CR^2CR^3=CR^4C(=X^1)NR^5R^6$$

or a salt thereof, wherein Q is an monocyclic aromatic ring, or Q is a dihalovinyl group or a group $R^7-C\equiv C-$ where $R^7$ is $C_{1-4}$ alkyl, tri $C_{1-4}$ alkylsilyl, halogen or hydrogen; $Q^1$ is a 1,2-cyclopropyl ring optionally substituted by one or more groups selected from $C_{1-3}$ alkyl, halo, $C_{1-3}$haloalkyl, alkynyl, or cyano; $R^1$, $R^2$, $R^3$ and $R^4$ are the same or different with at least one being hydrogen and the others being independently selected from hydrogen, halo, $C_{1-4}$ alkyl or $C_{1-4}$haloalkyl; $X^1$ is oxygen or sulphur; $R^5$ is $C_{1-8}$ hydrocarbyl optionally substituted, halo, cyano, trifluoromethyl, trifluoromethylthio or $C_{1-6}$ alkoxy; and $R^6$ is selected from:

(A) $-Y=X^2-(R^8)_a$ where $X^2$ is O or S, Y is carbon, $R^8$ is hydrogen, $C_{1-4}$ alkyl, $C_{1-4}$ alkoxy, $C_{1-5}$ alkylcarbonyl or aryl or $CO_2R^9$ where $R^9$ is an $C_{1-4}$ alkyl or aryl, and a is 1 or 2;

(B) $-CR^{15}R^{16}X^3R^{17}$ where $R^{15}$ and $R^{16}$ are hydrogen or $C_{1-4}$ alkyl, $X^3$ is oxygen or sulphur and $R^{17}$ is $C_{1-4}$ alkyl, $C_{1-5}$ alkylcarbonyl or aralkylcarbonyl $R^{17},R^{15}X^3$, their preparation, pesticidal compositions containing them and their use against pests.

8 Claims, No Drawings

CERTAIN 2,4-PENTADIENAMIDE PESTICIDES

This invention relates to pesticidal compounds, processes for their preparation, compositions containing them and to their use in the treatment of pests.

Unsaturated amides having a $C_{1-10}$ alkylene chain optionally including oxygen atoms are known as pesticides having various terminating groups which include within their scope optionally substituted phenyl (European Application Nos. 228222, 194764, 225011, Japanese Application No 57-212150, Meisters and Wailes: Aust. J. them. 1966, 19, 1215, Vig et al : J. Ind. Chem. Soc. 1974, 51(9), 817) or pyridyl (European Application 269457) or fused bicyclic ring systems (European Application Nos. 143593, 228853), or dihalovinyl or optionally substituted ethynyl (European Application 228222) groups.

Novel unsaturated amides having a 1,2-cyclopropyl ring adjacent to the diene unit linking the latter to a terminal group selected from optionally substituted monocyclic aromatic or fused bicyclic ring system, dihalovinyl or optionally substituted ethynyl have interesting pesticidal properties and are described in European Patent Application No. 893 11815.8.

Such compounds are secondary amides in which the N substituents are generally hydrogen and an alkyl group. It has now been found that certain tertiary amides, generally having a heteroatom or a carbon bearing a heteroatom attached to the amide nitrogen, have pestictdal activity.

Accordingly, the present invention provides a compound of formula (I):

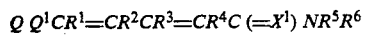

$$Q\;Q^1CR^1\!\!=\!\!CR^2CR^3\!\!=\!\!CR^4C\,(\!=\!X^1)\,NR^5R^6 \qquad (I)$$

or a salt thereof, wherein Q is an monocyclic aromatic ring, or fused bicyclic ring system of which at least one ring is aromatic containing 9 or 10 atoms of which one may be nitrogen and the rest carbon each ring system being optionally substituted, or Q is a dihalovinyl group or a group $R^7$—C≡C— where $R^7$ is $C_{1-4}$ alkyl, tri $C_{1-4}$ alkylsily, halogen or hydrogen; $Q^1$ is a 1,2-cyclopropyl ring optionally substituted by one or more groups selected from $C_{1-3}$ alkyl, halo, $C_{1-3}$ haloalkyl, alkynyl, or cyano; R1, $R^2$, $R^3$ and $R^4$ are the same or different with at least one being hydrogen and the others being independently selected from hydrogen, halo, $C_{1-4}$ alkyl or $C_{1-4}$haloalkyl; $X^1$ is oxygen or sulphur; $R^5$ is $C_{1-8}$ hydrocarbyl optionally substituted by dioxalanyl, halo, cyano, trifluoromethyl, trifluoromethylthio or $C_{1-6}$ alkoxy; and $R^6$ is selected from:

(A) —Y=$X^2$—$(R^8)_a$ where $X^2$ is O or S, Y is phosphorus or carbon, $R^8$ is hydrogen, $C_{1-4}$ alkyl, $C_{1-4}$ alkoxy, $C_{1-5}$ alkylcarbonyl or aryl or $CO_2R^9$ where $R^9$ gis an $C_{1-4}$ alkyl or aryl and a is 1 or 2

(B) —$S(O)_bR^{10}$ where $R^{10}$ is an $C_{1-4}$ alkyl, aryl, aryloxy or $C_{1-4}$ alkoxy, wherein the aryl ring may be substituted by one or more halo, nitro, cyano, $C_{1-4}$ alkyl, $C_{1-4}$ alkoxy groups each in turn optionally substituted by one or more halogens, or $R^{10}$ is a group $NR^{11}R^{12}$ wherein $R^{11}$ is —$COR^{13}$ where $R^{13}$ is hydrogen, fluorine or $C_{1-4}$ alkyl or $R^{13}$ is a group $CO.CO_2R^9$,SNR-11aR11b or P(→O)$R^8$ wherein $11^a$ and $11^b$ are the same or different and each is a group $R^{11}$ and $R^8$, $R^9$ and $R^{11}$as hereinbefore defined, or $R^{11}$ is $C_{1-4}$ alkyl substituted by $C_{1-4}$ alkyl, $C_{1-5}$ alkylcarbonyl or aryl, carboalkoxy or cyano, or $R^{11}$ is a group $CO_2R^{14}$ where $R^{14}$ is $C_{1-4}$ alkyl or aryl, $R^{12}$ is $C_{1-4}$ alkyl, and b=0, 1 or 2.

(C) —$CR^{15}R^{16}X^3R^{17}$ where $R^{15}$ and $R^{16}$ are hydrogen or $C_{1-4}$ alkyl, $X^3$ is oxygen or sulphur and $R^{17}$ is $C_{1-4}$ alkyl, $C_{1-5}$ alkylcarbonyl or aralkylcarbonyl $R^{17}$, $R^{15}X^3$ may be linked to form a ring system.

(D) —$CR^{15}R^{16}X^3$ is a 5 or 6 membered heterocyclic ring containing an oxygen or sulphur atom optionally substituted by $C_{1-4}$ alkyl.

By the term aryl is meant a carbocyclic or heterocyclic aromatic ring containing 5-10 ring atoms, preferably phenyl or pyridyl.

When Q is a monocyclic aromatic ring, this is suitably phenyl, pyridyl or thienyl and preferably phenyl. When Q is a bicyclic ring system, this is preferably naphthyl.

When Q contains an aromatic system, suitable substituents include one to four groups selected from $C_{1-6}$ hydrocarbyl, $C_{1-6}$ alkoxy or methylenedioxy, each optionally substituted by one to three halos, or from halo cyano or nttro or the substituent is a group $S(O)_nR^{18}$ wherein n is 0, 1 or 2 and $R^{18}$ is $C_{1-6}$ alkyl optionally substituted by one or more halos or $R^{18}$ is amino optionally substituted by one or two $C_{1-6}$ alkyl groups or the substttuent is a group $NR^{19}R^{20}$ where $R^{19}$ and $R^{20}$ are independently selected from hydrogen, $C_{1-6}$ alkyl or a group $COR^{21}$ where $R^{21}$ is $C_{1-6}$ alkyl.

The Q ring system normally contains up to three substituents and is suitably unsubstituted or substituted by one, two or three substituents such as halo or $C_{1-4}$ haloalkyl such as trifluoromethyl. The substitution of the Q ring system depends upon the nature of this ring system but is preferably at the 3, 4 or 5 positions when Q is a 6-membered ring.

Suitably $R^1$, $R^2$, $R^3$ and $R^4$ are chosen from hydrogen, methyl or fluoro. Suitably the stereochemistry of the double bonds is (E). Suitably when $R^2$ or $R^4$ is fluoro then the stereochemistry of the double bond to which $R^2$ or $R^4$ is attached is (Z).

Preferably $R^1$ is hydrogen, $R^2$ is hydrogen or fluoro, $R^4$ is hydrogen or fluoro and $R^3$ is hydrogen or $C_{1-4}$ alkyl, most preferably methyl.

Preferably the steric configuration of $Q^1$ in the chain is such that the substituents are attached to the ring to give trans geometry. Preferably the 3-position of the cyclopropyl ring is unsubstituted. Suitable substituents at the 1- and 2-positions of the cyclopropyl ring include fluoro, chloro, methyl or trifluoromethyl. Preferably the 1- position is unsubstituted and the 2- position is unsubstituted or substituted by fluoro or chloro.

Preferably $X^1$ is oxygen.

Suitably $R^5$ is $C_{1-4}$ alkyl optionally substituted by $C_{2-7}$ cycloalkyl, dioxalanyl, or $^5$ is $C_{2-5}$ alkenyl. Most suitably $R^5$ is branched chain $C_{4-6}$ alkyl group, such as isobutyl, 1,2-dimethylpropyl, 1,1,2-trimethyl propyl, 2,2-dimethylpropyl or $R^5$ is 2-methylprop-2-enyl or (2-methyl-1,3- dioxalan-2-yl) methyl. Preferably $R^5$ is isobutyl or 2-methyl-prop-2- enyl where $R^1$ and $R^2$ are hydrogen, $R^3$ is methyl and $R^4$ is hydrogen.

Suitably $R^6$ is selected from group (A) where $X^2$ is oxygen, Y is carbon or phosphorous and $R^8$ is hydrogen $C_{1-4}$ alkoxy or $CO_2R^9$ where $R^9$ is $C_{1-4}$ alkyl or aryl, and a is either 1 or 2, or group (B) where b is 0 and $R^{10}$ is aryl or a group $N(CH_3)R^{11}$ wherein $R^{11}$ is CHO or $CO_2$alkyl or group (C) where $R^{15}$ and $R^{16}$ are hydrogen, $X^3$ is oxygen and $R^{17}$ is $C_{1-4}$ alkyl.

Preferably $R^6$ is selected from a group (A) where $X^2$ is oxygen, Y is carbon or phosphorous and $R^8$ is $C_{1-4}$ alkoxy or $CO_2R9$ where $R^9$ is $C_{1-4}$alkyl or aryl and a is 1 or 2, or group (B) where b is 0 and $R^{10}$ is aryl or a group $N(CH_3)R^{11}$ wherein $R^{11}$ is CHO or $CO_2$ alkyl.

Preferably Y is carbon $R^8$ is $CO_2R^9$ wherein $R^9$ is an hereinbefore defined and a is 1.

Preferably $R^{10}$ is aryl.

Suitably when $CR^{15}R^{17}X^3$ is a heterocyclic ring it is a tetrahydrofuran or a tetrahydropyran ring.

Preferred compounds of the formula (I) include those of formula (II)

$$Q Q^1 CH=CR^2CR^3=CHCON R^5R^6 \qquad (II)$$

wherein Q, $Q^1$, $R^2$, $R^3$, $R^5$ and $R^6$ are as hereinbefore described.

Preferred compounds of the formula (II) include those wherein Q is substituted phenyl, $Q^1$ is a trans 1,2-cyclopropyl ring, where the 2-position of the cyclopropyl ring is unsubstituted or substituted by fluoro or chloro, $R^3$ is methyl or hydrogen, $R^1$ is hydrogen, $R^2$ and $R^4$ are hydrogen or fluoro and $R^5$ is isobutyl or 1,2-dimethylpropyl or 2-methylprop-2-enyl, X is oxygen or sulphur and $R^6$ is as hereinbefore defined.

Thus, preferred compounds of the formula ( I ) include:

Preferred compounds:
- (±)-(2E,4E)-N-Isobutyl-N-phenylthio-5-[trans-2-(3,4-dichlorophenyl)-cyclopropyl]-3-methylpenta-2,4-dienamide.
- (±)-(2E,4E)-N-Isobutyl-N-phenylthio-5-[r-1-fluoro-2-c-(3,4-dichlorophenyl)cyclopropyl]-3-methylpenta-2-4-dienamide.
- (±)-(2E,4E) Ethyl N-isobutyl-N-{5-[trans-2-(3,4-dichlorophenyl)cyclopropyl]-3-methylpenta-2,4-dienoyl}oxamate
- (±)-(2E,4E) Phenyl N-isobutyl-N-{5-[trans-2-(3,4-dichlorophenyl)cyclopropyl]-3-methylpenta-2,4-dienoyl)oxamate
- (±)(2E/Z,4E)N-Isobutyl-N-phenylthio-5-[r-1-fluoro-2-c-(3,4-dibromophenyl)cyclopropyl]-2-fluoro-3-methylpenta-2,4-dienamide
- (±)(2Z/E,4E)N-(2-Methylprop-2-enyl)-N-phenylthio-5-[r-1-fluoro-2-c-( 3-4-dibromophenyl)cyclopropyl]-3-methylpenta-2,4-dienamide
- (±)(2E,4E)N-Isobutyl-N-phenylthio-5-[r-1-chloro-2-c-(3,4-dichlorophenyl) cyclopropyl]-3-methylpenta-2,4-dienamide
- (±)(2E,4E)-N-Isobutyl-M-(2-methylphenyl)-thio-5-[r-1-fluoro-2-c-(3,4,dichlorophenyl) cyclopropyl]-3-methylpenta-2,4- dienamide
- (±)(2E,4E)N-Isobutyl-N-(4-chlorophenyl)thio-5-[r-1-fluoro-2-c-(3,4-dichlorophenyl) cyclopropy]-3-methylpenta-2,4-dienamide
- (±)(2E,4E)N-Isobutyl-N(4-t-butylphenyl)thio-5-[r-1-fluoro-2-c-(3,4-dichlorophenyl) cyclopropyl]-3-methyl-penta-2,4-dienamide
- (±)(2E/Z,4E)N-Isobutyl-N-2-pyridylthio-5-[r-1-fluoro-2-c-(3,4-dichlorophenyl)cyclopropyl]-3-methylpenta-2,4-dienamide By the term halo is meant fluoro, chloro, bromo and iodo. By the term hydrocarbyl group is meant, alkyl, alkenyl, alkynyl, aralkyl including a cyclic alkyl or alkenyl group optionally substituted by alkyl, alkenyl or alkynyl; and alkyl or alkenyl substituted by cyclic alkyl and alkenyl, and phenyl groups.

Salts of the compounds of the present invention will normally be acid addition salts. Such salts may be formed from mineral or organic or cycloalkyl acids. Preferred salts include those formed from hydrochloric, hydrobromic, sulphuric, citric, nitric, tartaric, phosphoric, lactic, benzoic, glutamic, aspattic, pyruvic, acetic, succinic, fumaric, maleic, oxaloacetic, hydroxy-naphthoic, isethionic, stearic, methane-sulphonic, ethanesulphonic, benzenesulphonic, toluene-p-sulphonic, lactobionic, glucuronic, thiocyanic, propionic, embonic, naphthenoic and perchloric acids.

The compounds of formula (I) may exist in a number of stereoisomeric forms. The present invention encompasses both individual geometric and stereoisomers and mixtures thereof. The present invention also encompasses compounds of the formula (I) containing radioisotopes, particularly those in which one to three hydrogen atoms are replaced by tritium or one or more carbon atoms are replaced by $^{14}C$.

In a further aspect, the present invention provides a process for the preparation of a compound of the formula (I) as hereinbefore defined which comprises:

(a) when $X^1$ is oxygen by reaction of a compound of formula $M^1NR^5R^6$ with a compound of formula (III)

$$QQ^1CR^1=CR^2CR^3=CR^4(C=X^1)B^1 \qquad (III)$$

where $B^1$ is a leaving group such as chlorine and $M^1$ is hydrogen or preferably a metal e.g. lithium, or by reaction of a compound of formula $R^6B^2$ with a compound of formula (IV)

$$QQ^1CR^1=CR^2CR^3=CR^4(C=X^1)NR^5R^{22} \qquad (IV)$$
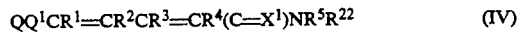

Where $R^{22}$ is hydrogen or preferably trialkylstlyl and $B^2$ is a leaving group.

Process (a) is normally carried out at a reduced temperature, for example between $-70°$ and $0°$ and in anhydrous aprotic solvent, such as an ether, e.g. tetrahydrofuran. The precise conditions are dependent on the nature of $R^6$, for example when $R^6$ ts SPh the reaction is conveniently carried out at $-60°$. The compounds of formula (III) are prepared, for example, by reaction of a carboxylic acid with oxalyl chloride in an anhydrous aprotic solvent such as dichloromethane in the presence of a catalyst e.g. N,N-dimethylformamide. Compounds of formula $M^1NR^5R^6$ are prepared by reaction of a base e.g. n-butyllithium with the amine $HNR^5R^6$ at reduced temperature (e.g. $-60°$) in an anhydrous aprotic solvent such as tetrahydrofuran.

Process (b) is carried out in an aprotic solvent such as an ether, e.g. tetrahydro-furan in the absence of moisture. If $R^{22}$ is trialkylsilyl, then compounds of formula (IV) may be prepared from the corresponding secondary amides by reaction with a silylating agent such as bis-tri-methylsilyl acetamide in an aprotic solvent such as acetonitrile or pyridine in the absence of moisture. If $R^{22}$ is hydrogen then compound of formula (IV) treated first with a base, for example n-butyl lithium and lithium diisopropylamide, before reaction with compound of formula $R^6B^2$.

Alternatively compounds of formula (IV) may be prepared by reaction of a compound of formula (III) with a compound of formula $M^1NR^5R^{22}$ where $M^1, R^5$ and $R^{22}$ are as hereinbefore defined.

The aforementioned secondary amides may be prepared by any of the routes detailed in the patent applications noted above.

The aforementioned carboxylic acids, precursors to compounds of formula (III) may be obtained by hydrolysis of the corresponding esters. The latter may be obtained by a number of alternative routes.

(i) a conventional Witrig or Wadsworth-Emmons reaction, using for example an aldehyde and ethoxycarbonylmethylene triphenylphosphorane or an anion from tetethylphosphonocrotonate or 3-methyl triethylphosphonocrotonate. This latter reaction may result in an isomeric mixture, for example a mixture of (Z) and (E) substituted dienoates; such a mixture may be reacted as above, and the resulting mixture of amides separated by chromatography or other convenient techniques. The Witrig-type reagent may be produced for example by the following route or a modification thereof:

(1)

$(CH_3)_2C=CHCO_2Et \longrightarrow$ (2)

(3)

$Z^2CH_2C(CH_3)=CHCO_2Et \longrightarrow$

Wittig/Wadsworth-Emmons reagent wherein $Z^2=(aryl)_3P$, $(aryl)_2P(O)$ or $(C_{1-4} alkoxy)_2$-P(O) where aryl is preferably phenyl and alkoxy is preferably ethoxy.
(1) N-bromo succinimide
(2) e.g. $(EtO)_3P$ or $(Ph)_3P$
(3) This reaction is normally carried out in the presence of a base such as lithium diisopropylamide, butyllithium, sodium alkoxide or sodium hydride.

(ii) by rearrangement and elimination of $HS(O)Z^3$ from a compound of formula:

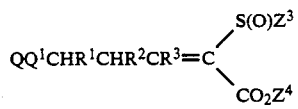

wherein $Q,Q^1$, $R^1$, $R^2$ and $R^3$ are as hereinbefore defined, $Z^3$ is any suitable group, e.g. phenyl, substituted phenyl such as 4-chlorophenyl or $C_{1-4}$ alkyl, for example methyl, $Z^4$ is $C_{1-4}$ alkyl, e.g. methyl or ethyl.

The above compound may be obtained by reaction of a compound $QQ^1CHR^1CHR^2CR^{30}$ with a compound $Z^3 S(O)CH_2CO_2Z^4$.

(iii) By elimination on a compound $QQ^1CHR^1CR^2(OZ^5)CR^{3'}CR^4CO_2Z^4$ wherein $Q,Q^1$, $R^1$, $R^2$, $R^3$, $R^4$ and $Z^4$ are as defined above, and $Z^5$ is hydrogen or $C_{1-4}$ acyl such as acetyl. The reaction is preferably carried out in an aromatic solvent, conveniently in the presence of a molybdenum catalyst and a base, such as bis-trimethylsilylacetamide.

The above compound may be obtained by the reaction of a suitable aldehyde with a suitable sulphenyl compound, followed by acylation.

(iv) reaction of a compound of formula $QQ^1CR^1=CR^2C(=O)R^3$ with one of formula $Me_3$-$SiCHR^4CO_2Z^4$ wherein $Q,R^1$ to $R^4$, $Q^1$ and $Z^4$ are as hereinbefore defined.

This process may be carried out in an anhydrous solvent, e.g. tetrahydrofuran in the absence of oxygen, in the presence of a base, e.g. lithium cyclohexyltsopropylamide.

(v) by reaction of a compound of formula $QQ^1CR^1=CR^2C(OZ^6)=CR^4CO_2Z^4$ with a compound of formula $R^3M^2$ wherein $Q,Q^1$, $R^1$, $R^2$, $R^3$, $R^4$ and $Z^4$ are as hereinbefore defined, $Z^6$ is a suitable group such as dialkylphosphate or trifluoromethanesulphonate and $M^2$ is a metal such as copper (I) or copper (I) associated with lithium or magnesium.

This process can be performed at low temperature in an anhydrous ethereal solvent such as diethyl ether, dimethyl sulphide or tetrahydrofuran in the absence of oxyEen.

(vi) by reaction of a compound of formula $QQ^1CR^1=CR^2M^3$ with one of formula $Y CR^3=CR^4CO_2Z^4$ wherein $Q,Q^1$, $R^1$, $R^2$, $R^3$, $R^4$ and $Z^4$ hereinbefore defined, Y is halo or tin and $M^3$ is a silyl or metal containing group, such as trimethylsilyl or a group containing zirconium, tin, aluminum or zinc, for example a bis(cyclopentadienyl) zirconium chloride group. This process is normally carried out at a non-extreme temperature i.e. between 0° and 100° C. and conveniently at room temperature, in a non-aqueous ethereal solvent such as tetrahydrofuran, in the presence of a palladium (O) catalyst, (such as his (triphenylphosphine)palladium) and under an inert atmosphere of nitrogen or argon.

(vii) by elimination of $Z^3S(O)H$ from a compound of formula

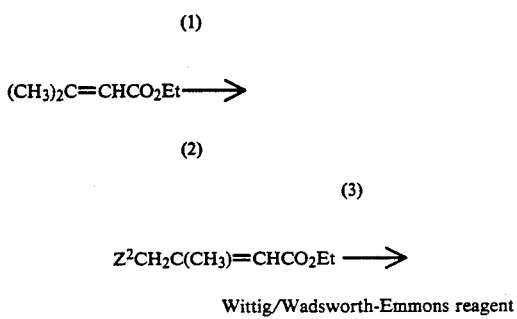

wherein Q, $Q^1$, $R^1$, $R^2$, $R^3$, $R^4$, $Z^3$ and $Z^4$ are as hereinbefore defined.

The above compound may be obtained by reaction of a compound $QQ^1CHR^1CR^2=CHR^3$ with $Z^3S(O)CH_2CO_2Z^4$ Process (b) may be carried out by having an aidehyde or ketone group attached either to the amide/thioamide terminus or to the $QQ^1$ fragment of formula (I) and then reacting this with the appropriate phosphorous ylid.

i.e.

$QQ^1(CR^1 = CR^2)COR^3 + Z^2CHR^4.C(=X^1)NHR^5$ or
$QQ^1COR^1 + Z^2CHR^2.CR^3 = CR^4.C(=X^1)NHR^5$ or
$QQ^1(CR^1 = CR^2)CHR^4Z^2 + R^4CO.C(=X^1)NH.R^5$ wherein Q, $Q^1$, $R^1$, $R^2$, $R^3$, $R^4$, $R^5$, $X^1$ and $Z^2$ are as hereinbefore defined.

Process (b) is carried out in an anhydrous inert solvent, for example an ether such as tetrahydrofuran, optionally in the presence of a base for example an amine derived from the preparation of the phophorous ylid, i.e. tsopropylamine, and preferably in the absence of oxygen, e.g. under a nitrogen atmosphere, at a low temperature ($-60°$ to 20° C.). The phosphorous ylid may be obtained from its precursor as described above by reaction with a base such as lithium diisopropylamide, butyllithium, sodium alkoxtde or sodium hydride. Compounds of the formula (I) wherein X is sulphur are preferably prepared by process (b) when $Z^2$ is a group $(C_{1-4}$ alkoxy$)_2P=0$. The aldehyde intermediates $QQ^1CR^1=0$ may be prepared by acid hydrolysis of a ketal, enol ether or acetal in a solvent such as acetone-water or by oxidation of the appropriate alcohols using for example pyrtdinium chlorochromate, pyridinium dichromate or oxalyl chloride-dimethyl sulphoxide in a solvent such as dichloromethane. The aldehydes may also be prepared by reduction of the appropriate nitriles with a reagent such as diisobutylaluminium hydride in hexane.

The alcohols may be prepared by
a) Reaction of QCH-CX$^4$OH with (Z$^7$)$_2$M$^2$ and CH$_2$X$_2^5$ where X$^4$ is a group such as hydrogen, fluoro, chloro or methyl X$^5$ is a halogen such as iodine, Z$^7$ is C$_{1-4}$ alkyl group such as ethyl and M$^2$ a metal such as zinc, in an inert solvent such as hexane or dichloromethane at moderate temperature ($-20°$ to $+20°$) and CH$_2$ and CH=CX$^4$ combine to form Q$^1$.
b) Reaction of QCH=CX$^4$CH$_2$OH with CX$_2^5$X$^6$CO$_2$M$^4$ where X$^5$ and X$^6$ are halogens such as fluorine and chlorine and M$^4$ is an alkali metal such as sodium in an inert solvent such as diglyme at moderate/elevated temperatures ($150°$-$200°$) and CX$_2^5$ and CH=CX$^4$combine to form Q$^1$.

The intermediate alcohols may be prepared by reduction of the ester QCH=CX$^4$CO$_2$Z$^4$ with for instance diisobutylalumintum hydride in an inert solvent such as dichloromethane or tetrahydrofuran at moderate temperature ($-20°$ to $25°$).

c) Reduction of an ester QQ$^1$CO$_2$Z$^4$, or of the appropriate carboxylic acid with for instance diisobutylalumtnium hydride or diborane in an inert solvent such as dichloromethane or tetrahydrofuran at moderate temperature ($-20°$ to $25°$). The esters may be prepared by reaction of a diazoacetate N$_2$CH.CO$_2$Z$^4$ with a compound QCH=CH$_2$ in the presence of a copper containing catalyst such as copper sulphate where CH and CH=CH$_2$ combine to form Q$^1$. The esters may also be prepared by the reaction of QCH=CHCO$_2$Z$^4$ with an ylid derived from Me$_2$S$^+$-(O)$_m$C$^-$(Z$^7$)$_2$ where Z$^7$ is hydrogen or C$_{1-6}$ alkyl and m is 0 or 1.

The compounds of formula (I) may be used to control pests such as arthropods e.g. insect and acarine pests. and helminths, i.e. nematodes. Thus, the present invention provides a method for the control of arthropods and/or helminths which comprises administering to the arthropod and/or helminth or to their environment an arthropodically effective amount of a compound of the formula (I). The present invention also provides a method for the control and/or eradication of arthropod and/or helminth infestations of animals (including humans) and/or of plants,(including trees) and/or stored products which comprises administering to the animal or locus an effective amount of a compound of the formula (I). The present invention further provides for the compounds of the formula (I) for use in human and veterinary medicine, in public health control and in agriculture for the control of arthropod and/or helminth pests.

The compounds of formula (I) are of particular value in the protection of field, forage, plantation, glasshouse, orchard and vineyard crops, of ornamentals and of plantation and forest trees, for example, cereals (such as maize, wheat, rice, sorghum), cotton, tobacco, vegetables and salads (such as beans, cole crops, curcurbits, lettuce, onions, tomatoes and peppers), field crops (such as potato, sugar beet, ground nuts, soyabean, oil seed rape), sugar cane, grassland and forage (such as maize, sorghum, lucerne), plantations (such as of tea, coffee, cocoa, banana, oil palm, coconut, rubber, spices), orchards and groves (such as of stone and pip fruit, citrus, kiwifruit, avocado, mango, olives and walnuts), vineyards, ornamental plants, flowers and shrubs under glass and in gardens and parks, forest trees (both deciduous and evergreen) in forests, plantations and nurseries.

They are also valuable in the protection of timber (standing, felled, converted, stored or structural) from attack by sawflies (e.g. Urocerus) or beetles (e.g. scolytids, platypodids, lyctids, bostrychtds, cerambycids, anobiids).

They have applications in the protection of stored products such as grains, fruits, nuts, spices and tobacco, whether whole, milled or compounded into products, from moth, beetle and mite attack. Also protected are stored animal products such as skins, hair, wool and feathers in natural or converted form (e.g. as carpets or textiles) from moth and beetle attack; also stored meat and fish from beetle, mite and fly attack.

The compounds of general formula (I) are of particular value in the control of arthropods or helminths which are injurious to, or spread or act as vectors of diseases in man and domestic animals, for example those hereinbefore mentioned, and more especially in the control of ticks, mites, lice, fleas, midges and biting, nuisance and myiasis flies.

The compounds of Formula (I) may be used for such purposes by application of the compounds themselves or in diluted form in known fashion as a dip, spray, fog, lacquer, foam, dust, powder, aqueous suspension, paste, gel, cream, shampoo, grease, combustible solid, vapourising mat, combustible coil, bait, dietary supplement, wettable powder, granule, aerosol, emulsifiable concentrate, oil suspensions, oil solutions, pressure-pack, impregnated article, pour on formulation or other standard formulations well known to those skilled in the art. Dip concentrates are not applied per se, but diluted with water and the animals immersed in a dipping bath containing the dip wash. Sprays may be applied by hand or by means of a spray race or arch. The animal, soil, plant or surface being treated may be saturated with the spray by means of high volume application or superficially coated with the spray by means of light or ultra low volume application. Aqueous suspensions may be applied in the same manner as sprays or dips. Dusts may be distributed by means of a powder applicator or, in the case of animals, incorporated in perforated bags attached to trees or rubbing bars. Pastes, shampoos and greases may be applied manually or distributed over the surface of an inert material, such as that against which animals rub and transfer the material to their skins. Pour-on formulations are dispensed as a unit of liquid of small volume on to the backs of animals such that all or most of the liquid is retained on the animals.

The compounds of Formula (I) may be prepared either as formulations ready for use on the animals, plants or surface or as formulations requiring dilution prior to application, but both types of formulation comprise a compound of Formula (I) in intimate admixture with one or more carriers or diluents. The carriers may be liquid, solid or gaseous or comprise mixtures of such substances, and the compound of Formula (I) may be present in a concentration of from 0.025 to 99% w/v depending upon whether the formulation requires further dilution.

Dusts, powders and granules and other solid formulations comprise the compound of Formula (I) in intimate admixture with a powdered solid inert carrier for example suitable clays, kaolin, bentoniic, attapulgite, adsorbent carbon black, talc, mica, chalk, gypsum, tricalcium phosphate, powdered cork, magnesium siliate, vegetable carriers, starch and diatomaceous earths. Such solid formulations are generally prepared by impregnating the solid diluents with solutions of the compound of formula (I) in volatile solvents, evaporating the solvents and, if desired grinding the products so as to obtain powders and, if desired, granulating, compacting or encapsulating the products.

Sprays of a compound of Formula (I) may comprise a solution in an organic solvent (e.g. those listed below) or an emulsion in water (dip wash or spray wash) prepared in the field from an emulsifiable concentrate (otherwise known as a water miscible oil) which may also be used for dipping purposes. The concentrate preferably comprises a mixture of the active ingredient, with or without an organic solvent and one or more emulsifiers. Solvents may be present within wide limits but preferably in an amount of from 0 to 90% w/v of the composition and may be selected from kerosene, ketones, alcohols, xylene, aromatic naphtha, and other solvents known in the formulating art. The concentration of emulsifiers may be varied within wide limits but is preferably in the range of 5 to 25% w/v and the emulsifiers are conveniently non-ionic surface active agents including polyoxyalkylene esters of alkyl phenols and polyoxyethylene derivatives of hexitol anhydrides and anionic surface active agents including Na lauryl sulphate, fatty alcohol ether sulphates, Na and Ca salts of alkyl aryl sulphonates and alkyl sulphosuccinates. Cationic emulsifiers include benzalkonium chloride and quaternary ammonium ethosuphates.

Amphoteric emulsifiers include carboxymethylated oleic imidazoline and alkyl dimethyl betain.

Vaporising mats normally comprise cotton and cellulose mix compressed into a board of approximately 35×22×3 mm dimensions, treated with up to 0.3 ml of concentrate comprising the active ingredient in an organic solvent and optionally an antioxidant, dye and perfume. The insecticide is vaporised using a heat source such as an electrically operated mat heater.

Combustible solids normally comprise of wood powder and binder mixed with the active ingredient and formed into shaped (usually coiled) strips. Dye and fungicide may also be added. Wettable powders comprise an inert solid carrier, one or more surface active agents, and optionally stabilisers and/or anti-oxidants.

Emulsifiable concentrates comprise emulsifying agents, and often an organic solvent, such as kerosene, ketones, alcohols, xylenes, aromatic naphtha, and other solvents known in the art.

Wettable powders and emulsifiable concentrates will normally contain from 5 to 95% by weight of the active ingredient, and are diluted, for example with water, before use.

Lacquers comprise a solution of the active ingredient in an organic solvent, together with a resin, and optionally a plasticiser.

Dip washes may be prepared not only from emulsiftable concentrates but also from wettable powders, soap based dips and aqueous suspensions comprising a compound of Formula (I) in intimate admixture with a dispersing agent and one or more surface active agents.

Aqueous suspensions of a compound of Formula (I) may comprise a suspension in water together with suspending, stabilizing or other agents. The suspensions or solutions may be applied per se or in a diluted form in known fashion.

Greases (of ointments) may be prepared from vegetable oils, synthetic esters of fatty acids or wool fat together with an inert base such as soft paraffin. A compound of Formula (I) is preferably distributed uniformly through the mixture in solution or suspension.

Greases may also be made from emulsifiable concentrates by diluting them with an ointment base.

Pastes and shampoos are also semi-solid preparations in which a compound of Formula (I) may be present as an uniform dispersion in a suitable base such as soft or liquid paraffin or made on a non-greasy basis with glycerin, mucilage or a suitable soap. As greases, shampoos and pastes are usually applied without further dilution they should contain the appropriate percentage of the compound of Formula (I) required for treatment.

Aerosol sprays may be prepared as a simple solution of the active ingredient in the aerosol propellant and co-solvent such as halogenated alkanes and the solvents referred to above, respectively. Pour-on formulations may be made as a solution or suspension of a compound of Formula (I) in a liquid medium. An arian or mammal host may also be protected against tnfestation of acarine ectoparasites by means of carrying a suitably-moulded, shaped plastics article impregnated with a compound of Formula (I). Such articles include impregnated collars, tags, bands, sheets and strips suitably attached to appropriate parts of the body. Suitably the plastics material is a polyvinyl chloride (PVC).

The concentration of the compound of Formula (I) to be applied to an animal, premises or outdoor areas will vary according to the compound chosen, the interval between treatments, the nature of the formulation and the likely lnfestation, but in general 0.001 to 20.0% w/v and preferably 0.01 to 10% of the compound should be present in the applied formulation. The amount of the compound deposited on an animal will vary according to the method of application, size of the animal, concentration of the compound in the applied formulation, factor by which the formulation is diluted and the nature of the formulation but in general will lie in the range of from 0.0001% to 0.5% w/w except for undiluted formulations such as pour-on formulations which in general will be deposited at a concentration in the range from 0.1 to 20.0% and preferably 0.1 to 10%. The amount of compound to be applied to stored products in general will lie in the range of from 0.1 to 20 ppm. Space sprays may be applied to give an average initial concentration of 0.001 to 1mg of compound of formula (I) per cubic metre of treated space.

The compounds of formula (I) are also of use in the protection and treatment of plant species, in which case an effective insecticidal, acaricidal or nematocidal amount of the active ingredient is applied. The application rate will vary according to the compound chosen, the nature of the formulation, the mode of application, the plant species, the planting density and likely tnfestation and other like factors but in general, a suitable use rate for agricultural crops is in the range 0.001 to 3 kg/Ha and preferably between 0.01 and 1 kg/Ha. Typical formulations for agricultural use contain between 0.0001% and 50% of a compound of formula (I) and conveniently between 0.1 and 15% by weight of a compound of the formula (I).

Dusts, greases, pastes and aerosol formulations are usually applied in a random fashion as described above and concentrations of 0.001 to 20% w/v of a compound of Formula (I) in the applied formulation may be used.

The compounds of formula (I) have been found to have activity against the common housefly (*Musca domestica*). In addition, certain compounds of formula (I) have activity against other arthropod pests including *Myzus persicae, Tetranychus urticae, Plutella xylostella, Culex* spp. *Tribolium castaneum, Sitophilus granarius,*

*Periplaneta americana* and *Blattella germanica*. The compounds of formula (I) are thus useful in the control of arthropods e.g. insects and acarines in any environment where these constitute pests, e.g. in agriculture, in animal husbandry, in public health control and in domestic situations.

Insect pests include members of the orders Coleoptera (e.g. Anobium, Ceutorhynchus, Rhynchophorus, Cosmopolites, Lissorhoptrus, Meligethes, Hypothenemus, Hylesinus, Acalymma, Lema, Psylliodes, Leptinotarsa, Gonocephalum, Agriotes, Dermolepida, Heteronychus, Phaedon, Tribolium, Sitophilus, Diabrotica, Anthonomus or Anthrenus spp.), Lepidoptera (e.g. Ephestia, Mamestra, Earias, Pectinophora, Ostrinia, Trichoplusia, Pieris, Laphygma, Agrotis, Amathes, Wiseana, Tryporysa, Diatraea, Sporganothis, Cydia, Archips, Plutella, Chilo, Heliothis, Spodoptera or Tineola spp.), Diptera (e.g. Musca, Aedes, Anopheles, Culex, Glossina, Simulium, Stomoxys, Haematobia, Tabanus, Hydrotaea, Lucilia, Chrysomia, Callitroga, Dermatobia, Gasterophilus, Hypoderma, Hylemyia, Atherigona, Chlorops, Phytomyza, Ceratitis, Liriomyza and Melophagus spp.), Phthtraptera (Malophaga e.g. Damalina spp. and Anoplura e.g. Linognathus and Haematopinus spp.), Hemiptera (e.g. Aphis, Bemisia, Phorodon, Aeneolamia, Empoasca, Parkinsiella, Pyrilla, Aonidiella, Coccus, pseudococus, Helopeltis, Lygus, Dysdercus, Oxycarenus, Nezara, Aleurodes, Triatoma, Psylla, Mysus, Megourn, Phylloxera, Adelyes, Nilparvata, Nephrotetix or Cimex spp.), Orthoptera (e.g. Locusta, Gryllus, Schistocerca or Acheta spp.), Dictyoptera (e.g. Blattella, periplaneta or Blatta spp.), Hymenoptera (e.g. Athalia, Cephus, Atta, Solenopsis or Monomorium spp.), Isoptera (e.g. Odontotermes and Reticulitermes spp.), Siphonaptera (e.g. Ctenocephalides or Pulex spp.), Thysanura (e.g. Lepisma spp.), Dermaptera (e.g. Forficula spp.), Pscoptera (e.g. Peripsocus spp.) and Thysanoptera (e.g. Thrips tabaci),.

Acarine pests include ticks, e.g. members of the genera Boophilus, Ornithodorus, Rhipicephalus, Amblyomma, Hyalomma, Ixodes, Haemaphysalis, Dermacentor and Anocentor, and mites and manges such as Acarus, Tetranychus, Psorpptes, Notoednes, Sarcoptes, Psorergates, Chorloptes, Eutrombicula, Demodex, Panonychus, Bryobia, Eriophyes, Blaniuius, Polyphagotarsonemus, Scutigerella, and Oniscus spp.

Nematodes which attack plants and trees of importance to agriculture, forestry, horticulture either directly or by spreading bacterial, viral, mycoplasma or, fungal diseases of the plants, include root-knot nematodes such as Meloidogyne spp. (e.g. *M. incognita)*; cyst nematodes such as Globodera spp. *(e.g. G. rostochiensis)*; Heterodera spp. *(e.g. hydrogen. avenae)*; Radopholus spp. *(e.g. R. similis)*; lesion nematodes such as Pratylenchus spp. *(e.g. P. pratensis)*; Belonolaimus spp. *(e.g. B. gracilis)*; Tylenchulus spp. (e.g. *T. semipenetrans)*; Rotylenchulus spp. (e.g. *R. reniformis)*; Rotylenchus spp. (e.g. *R. robustus)*; Helicotylenchus spp. (e.g. hydrogen. multicinctus); Hemicycliophora spp. (e.g. hydrogen. gracilis); Criconemoides spp. (e.g. C. similis); Trichodorus spp. (e.g. *T. primttivus)*; dagger nematodes such as Xiphinema spp. (e.g. X. diversicaudatum), Longidorus spp (e.g. *L. elongatus)*; Hoplolaimus spp. (e.g. hydrogen. coronatus); Aphelenchoides spp. (e.g. *A. ritzema-bosi, A. besseyi)*; stem and bulb eelworms such as Ditylenchus spp. (e.g. *D. dipsaci)*.

Compounds of the invention may be combined with one or more other pesticidally active ingredients (for example pyrethroids, carbamates and organophosphates) and/or with attractants, repellents, bacteriocides, fungicides, nematocides, anthelmintics and the like. Furthermore, it has been found that the activity of the compounds of the invention may be enhanced by the addition of a synergist or potentiator, for example: one of the oxidase inhibitor class of synergists, such as piperonyl butoxide or propyl 2-propynylphenylphosphonate; a second compound of the invention; or a pyrethroid pesticidal compound. When an oxidase inhibitor synlergist is present in a formula of the invention, the ratio of synergist to compound of Formula (I) will be in the range 25:1–1:25 eg about 10:1.

Stabilisers for preventing any chemical degradation which may occur with the compounds of the invention include, for example, antioxidants (such as tocopherols, butylhydroxyanisole and butylhydroxytoluene) and scavengers (such as epichlorhydrin) and organic or inorganic bases e.g. trialkylamines such as triethylamine which can act as basic stabilises and as scavengers.

EXAMPLE 1

(±)-(2E,4E)-N-Isobutyl-N-phenylthio-5-[trans-2-(3,4-dichlorophenyl)cyclopropyl]-3-methylpenta-2.4-dienamide (i) 3,4-Dichlorocinnamic acid (6.5g) (Ex.Aldrich), dimethylsulphate (3.77 g), potassium carbonate (4.13 g) and anhydrous acetone heated together under reflux. After cooling and filtration the acetone was removed and the residue recrystallised (80:20-hexane: ether) to give methyl 3,4-dichlorocinnamate as a colourless solid (4 g).

(ii) The above ester (4 g) in dry dichloromethane (80 ml) treated with diisobutylaluminium hydride (35 ml at 1M in hexane) at −20°. Allowed to reach 0° and treated with saturated ammonium chloride and then dil. aqueous hydrochloric acid, the mixture was partitioned between diethyl ether and water and worked up in conventional fashion. The crude product was purified by chromatography (silica, 1:1 ether/hexane) to give 3-(3,4-dichlorophenyl) prop-2-en-1-ol as a colourless solid (3 g).

(iii) A solution of the above alcohol (3 g) in dry dichloromethane (50 ml) treated at 0° with diethyl zinc (30 ml at 1M in hexane) and diiodomethane (11.88 g). The reaction mixture was heated under gentle reflux for 3 hours, stirred at room-temperature for 2 hours. The reaction mixtures was quenched with aqueous ammonium chloride and then dilute hydrochloric acid. The reaction mixture was partitioned between ether and water, the organic phase was washed with aqueous sodium thiosulphate and brine and dried. The product purified by chromatography (silica, 80:20 hexane/ether) to give 2-(3,4-dichlorophenyl)cyclopropyl methanol (2.27 g) as a colourless oil.

(iv) The above alcohol (2.27 g) was added to the salt prepared from oxalyl chloride (1 ml) and dimethyl sulphoxide (1.63 ml) in dichloromethane. After 45 mins. at −60° triethylamine (7.3 ml) was added and the mixture allowed to reach 0°. After conventional work-up 1-formyl-2-(3,4-dichlorophenyl)cyclopropane (2.2 g) was obtained as a yellow oil. This was used directly without further purification.

(v) Lithium diisopropylamide, prepared from diisopropylamine (0.72 ml) and n-butyl lithium (3.2 ml at 1M in hexane) in anhydrous tetrahydrofuran, was treated with triethyl 3-methyl-4-phosphonocrotonate (5.11 mmol) (ex.Aldrich) at −60°. The reaction mixture was kept at −60° for 1 hour and the above aldehyde (5.11 mmol) added. The reaction mixture was kept at 0° for 16 hours then worked up in conventional fashion. The crude product was purified by chromatography (silica, 95:5 hexane/ether) to give (2E,4E) ethyl 5-[trans-2-(3,4-dichlorophenyl)cyclopropyl]-3-methylpenta-2,4-dienoate.

(vi) The above ester (2.5 g) in ethanol (40 ml) was treated with potassium hydroxide (1.35 g) in water (10 ml) at 55°–60° for 6 hours. The reaction mixture was concentrated and the residue partitioned between ether and water. The aqueous phase was acidified and extracted with ether (c.250 ml), after drying the volatiles were removed and the residue triturated with ether/hexane (1:1), (2E,4E) 5-[trans-2-(3,4-dichlorophenyl) cyclopropyl]-3-methyldienoic acid collected as a colourless solid (2 g).

(vii) Diphenyl disulphide (9.81 g) was added to a solution of silver nitrate (7.8 g) in methanol (400 ml). Isobutylamine (22.3 ml) was added with cooling and the mixture stirred at room temperature for 24 hours. After filtration the filtrate was concentrated and the crude product purified by short path distillation. (137° at 0.7mm) to give N-isobutyl phenylsulphenamide.

(viii) The above sulphenamide (242.5 mg) in anhydrous THF (5 ml) was treated at −60° with n-butyl lithium (837 μl) (1.6M in hexane). After 2 hours at −55° 5-[trans-2-(3,4-dichlorophenyl)cyclopropyl]-3-methyl-2,4-dienoyl chloride (prepared from the acid (398 mg. part vi), oxaiyl chloride (130 μl) and dimethylformamide (2 drops) in dichloromethane (5ml) in THF (4 ml) was added at −70°. The whole was stirred at −60° for 2 hours and worked up in conventional fashion. Purification of the crude material by chromatography (silica, hexane 80:20 hexane/ether) gave the title compound as a yellow oil (0.2 g).

EXAMPLE 2

(±) (2E,4E) Ethyl N-isobutyl-N-(5-[trans-2-(3,4-dichlorophenyl)cyclopropyl]-3-methylpenta-2,4-dienoyl]oxamate (i) Chlorotrimethylsilane (25 mmol) added at 0° to isobutylamine (50 mmol). The mixture was stirred at room temperature for 1 hour and at 100° for 1 hour. After dilution with anhydrous ether and filtration the organic phase was concentrated and the residue distilled under nitrogen to give N-trimethylsilyltsobutylamine (bp 128° at 760 mm).

(ii) The dienoyl chloride was prepared according to example 1 part (vii). (Acid, 199 mg; oxalyl chloride, 59 μl). A solution N-trimethylsilybutylamine (122 μl) in THF (4 ml) was treated with butyl lithium (419 μl at 1.6M in hexane) at −70°. The temperature was allowed to reach 0° and the mixture recooled to −70°. The dienoyl chloride in THF (3 ml) was added to the colourless suspension and kept at −70° for 0.5 hours when ethyl oxalyl chloride (ex. Lancaster, 75 μl) was added to the dark red solution. The reaction was kept for 16 hours at −10° and worked-up in conventional fashion. The crude product was purified by column chromatography (silica, 80:20 hexane/ether) to give the title compound as an amber oil (70 mg).

EXAMPLE 3

(±)(2E,4E) Phenyl N-isobutyl-N-(5-[trans-2-(3,4-dichlorophenyl)cyclopropyl]-3-methylpenta-2,4-dienoyl}oxamate Prepared by analogy with example 2 using phenyl oxalyl chloride (Prepared according to Simon & Seyfurth J.Org. Chem, 23,1078(1958)) in place of ethyl oxalyl chloride.

EXAMPLE 4

(±)(2E,4E) N-Isobutyl-N-phenylthio-5[r-1-fluoro-2-c-(3,4-dichlorophenyl)cyclopropyl]-3-methylpenta-2,4-dienamide A mixture of sodium hydride (0.33 g), diethyl oxalate (1.83 g), ethyl fluoroacetate (1.33 g) and anhydrous THF (10 ml) was heated under reflux for 4 hours whereupon 3,4-dichlorobenzaldehyde (2.18 g) (ex.Aldrich) in THF was added. After 18 hours at room temperature the reaction mixture was partitioned between water and ether and worked up in conventional fashion. Purification by chromatography (silica, 80:20 hexane/ether) gave (Z) ethyl 3-(3,4-dichlorophenyl)-2-fluoroprop-2-enoate (2.1 g.

The above ester was subjected to reduction as in example 1(ii) to give 3-(3,4-dichlorophenyl)-2-fluoroprop-2-en-1-ol..The latter (35 g) was subjected to cyclopropanation as in example 1(iii) to give 1-fluoro-2-(3,4-dichlorophenyl)cyclopropyl methanol (25 g). This was subsequently converted to 5-[r-1-fluoro-2-c-(3,4-dichlorophenyl)cyclopropyl]-3-methylpenta-2,4-dienoic acid (11 g) by analogy with example 1(iv)(v)-(vi). The above acid (398 mg) was converted by analogy with example 1(vii) to the title compound which was obtained after purification by chromatography as a yellow oil (0.18 g).

EXAMPLE 5

(±(2E/Z,4E)N-Isobutyl-N-phenylthio-5-[r-1-fluoro-2-c-(3-4-dibromophenyl) cyclopropyl]-2-fluoro-3-methylpenta-2,4-dienamide ±(2Z/E,4E)N-Isobutyl-5-[r-1-fluoro-2-c-(3,4-dibromophenyl)cyclopropy-1]-2-fluoro-3-methylpenta-2,4-dienamtde was prepared according to EP 0 369 762 (published 23.5.90). The latter (0.25 g) in tetrahydrofuran (3 ml) was treated with butyl lithium in hexane (324 μl @ 1.6M) at −70°. After 20 minutes phenylsulphenyl chloride (60.7 μl) was added. Mixture kept @−70° for 20 minutes and quenched with aqueous ammonium chloride. Conventional work-up gave a crude product which was purified by column chromatography (silica; ether/hexane) to give the title compound as a yellow oil.

EXAMPLE 6

(±)(2Z/E,4E)N-(2-Methylprop-2-enyl)-N-phenylthio-5-[r-1-fluoro-2-c-(3,4-dibromophenyl) cyclopropyl]-3-mathylpenta-2,4-dienamide Prepared by analogy with example 5 starting from (2Z/E,4E)N-(2-methylprop-2-enyl)-5-[r-1-fluoro-2-c-(3,4-dibromophenyl) cyclopropyl]-methylpenta-2,4-dienamide (EP 0 369 762).

EXAMPLE 7

(±)(2E,4E)N-Isobutyl-N-phenylthio 5-[r-1-chloro-2-c-(3,4-dichlorophenyl) cyclopropyl]-3-methylpenta-2,4-dienamide Prepared by analogy with example 1 starting from (2E,4E)N-isobutyl 5-[r-1-chloro-2-c-(3,4-dichlorophenyl)cyclopropyl-3-methylpenta-2,4-dienamide (EPO 369 762).

EXAMPLE 8

(±)(2E,4E)-n-Isobutyl-n-(2-methylphenyl)-thio-5-[r-1-fluoro-2-c-(3,4, dichlorophenyl)cyclopropyl]-3-methylpenta-2,4-dienamide N-Isobutyl 2-methylphenylsulphenamide was prepared as in example 1. 2-methylphenyldisulphide was obtained from 2-methylthiophenol (ex Aldrich) according to Davis et al., (J.Org. Chem., 42. 967, 1977). The title compound was prepaed by analogy with exaple 4.

EXAMPLE 9

(±)(2E,4E)N-Isobutyl-N-(4-chlorophenyl)thio-5-[r-1-fluoro-2-c-(3,4-dichlorophenyl) cyclopropyl]-3-methylpenta-2,4-dienamide.

N-Isobutyl 4-chlorophenylsulphenamide was prepared from 4-chloro-thiophenol (ex Aldrich) by analogy with examples 1 and 8 and the title compound prepared by analogy with example 4.

EXAMPLE 10

(±)(2E,4E)N-Isobutyl-N-(4-t-butylphenyl)thio-5-[r-1-fluoro-2-c-(3,4-dichlorophenyl) cyclopropyl]-3-methyl-penta-2,4-dienamide N-Isobutyl 4-butylphenylsulphenamide prepared from 4-t-butylthio-phenol (ex Fairfield) by analogy with examples 1 and 8 and converted to the title compound by analogy with example 4.

EXAMPLE 11

(±)(2E/Z.4E)N-Isobutyl-N-2-pyridylthio 5-[E-1-fluoro-2-c-(3,4-dichlorophenyl)cyclopropyl]-3-methylpenta-2,4-dienamide N-Isobutyl 2-pyridysulphenamide prepared from 2-pyridyldisulphide (ex Lancaster) by analogy with example 1 and converted to the title compound by analogy with example 4.

| Example No. | $^1$H NMR Data |
|---|---|
| 1. | 7.25(5H, m); 7.13(3H, m); 6.88(1H, d); 6.58(1H, s); 6.22 (1H, d); 5.68(1H, d of d); 3.50(2H, d); 2.18(3H, s); 2.11, 1.95, 1.70(3H, 3m); 1.24(2H, m); 0.91(6H, d). |
| 2. | 7.23(3H, m); 6.92(1H, d); 6.30(1H, d); 6.02(1H, s); 5.83(1H, d of d); 4.37(2H, q); 3.59(2H, d); 2.20 (3H, s); 2.04 (2H, m); 1.77(1H, m); 1.45(3H, t); 1.29 (2H m); 0.94(6H d). |
| 3. | 7.35(7H, m); 7.19(1H, s); 6.92(1H, d); 6.35(1H, d); 6.08 (1H, s); 5.85(1H, d of d); 3.66(2H, d); 2.26(3H, s); 2.08 (2H, m); 1.78(1H, m); 1.30(2H, m); 0.95(6H, d). |
| 4. | 7.36, 7.25, 7.08(8H, 3m); 6.68(1H, s); 6.39(1H, d); 5.83 (1H, d of d); 3.52(2H, d); 2.20, 2.13, 1.73, 1.52(4H, 4m), 2.19(3H, s); 0.93(6H, d). |
| 5. | 7.35(8H, m); 6.79(1H, d); 5.77(1H, d of d); 3.48(2H, d); 2.21(1H, m); 1.85(3H, s); 1.5–1.5(3H, m); 0.92(6H, d) |
| 6. | 7.30(8H, m); 6.71, 7.30(1.H, 2s); 6.41(1H, d); 5.86(1H, 2d of d)4.85(2H, d); 4.25(2H, s); 2.25(1H, m); 2.21, 1.71 (3H, 2s); 1.45-1.72(2H, m); 1.57(3H, s) |
| 7. | 7.25(8H, m); 6.69(1H, s); 6.43(1H, d); 5.85(1H, d); 3.50 (2H, d); 2.48(1H, t); 2.19(3H, s); 2.12, 1.75(3H, 2m); 0.92(6H, d) |
| 8. | 6.9–7.4(7H, m); 6.57(1H, s); 6.34(1H, d); 5.83(1H, d of d); 3.50(2H, d); 2.27(3H, s); 2.19(3H, s); 2.18(1H, m); 1.70, 1.51(3H, 2m); 0.95(6H, d) |
| 9. | 7.32, 7.08(7H, 2m); 6.67(1H, s); 6.36(1H, d); 5.85(1H, d of d); 3.52(2H, d); 2.28(1H, m); 2.20(3H, s); 2.12, 1.76, 1.56(3H, 3m); 0.93(6H, d) |
| 10. | 7.37, 7.07(7H, 2m); 6.71(1H, s); 6.40(1H, d); 5.86(1H, d of d); 3.50(2H, d); 2.27(1H, m); 2.19(3H, s); 2.12, 1.75, 1.54(3H, 3m); 1.33(9H, s); 0.92(6H, s) |
| 11. | 8.50(1H, m); 7.66, 7.46, 7.09(6H, m); 7.05, 6.99(1H, 2s); 6.56, 6.34(1H, 2d); 5.95, 5.81(1H, 2d of d); 3.44(2H, bd.d); 2.26(1H, m); 2.18, 1.97(3H, 2s); 2.13, 1.75, 1.56 (3H, m's); 0.95(6H, 2d) |

TLC Chromatography on Silica

| Example No. | Solvent (ether:hexane) | Rf value |
|---|---|---|
| 1. | 1:4 | 0.35 |
| 2. | 1:0 | 0.75 |
| 3. | 1:1 | 0.51 |
| 4. | 1:2 | 0.22 |
| 5. | 1:2 | 0.39 |
| 6. | 1:4 | 0.15 |
| 7. | 3:7 | 0.28 |
| 8. | 1:2 | 0.29 |
| 9. | 1:2 | 0.17 |
| 10. | 1:2 | 0.35 |
| 11. | 1:1 | 0.27 |

The following examples illustrate, in a non-limiting manner, preferred aspects of the invention.

Formulations

| 1. Emulsifiable Concentrate | |
|---|---|
| Compound of formula (I) | 10.00 |
| Alkyl phenol ethoxylate* | 7.50 |
| Alkyl aryl sulphonate* | 2.50 |
| $C_{8-13}$ aromatic solvent | 80.00 |
| | 100.00 |

| 2. Emulsifiable Concentrate | |
|---|---|
| Compound of formula (I) | 10.00 |
| Alkyl phenol ethoxylate* | 2.50 |
| Alkyl aryl sulphonate* | 2.50 |
| Ketonic solvent | 64.00 |
| $C_{8-13}$ aromatic solvent | 18.00 |
| Antioxidant | 3.00 |
| | 100.00 |

| 3. Wettable Powder | |
|---|---|
| Compound of formula (I) | 5.00 |
| $C_{8-13}$ aromatic solvent | 7.00 |
| $C_{18}$ aromatic solvent | 28.00 |
| China clay | 10.00 |
| Alkyl aryl sulphonate* | 1.00 |
| Napthalene sulphonic acid* | 3.00 |
| Diatomaceous earth | 46.00 |
| | 100.00 |

| 4. Dust | |
|---|---|
| Compound of formula (I) | 0.50 |
| Talc | 99.50 |
| | 100.00 |

| 5. Bait | |
|---|---|
| Compound of formula (I) | 0.5 |
| Sugar | 79.5 |
| Paraffin wax | 20.0 |
| | 100.00 |

6. Emulsion Concentrate

| Formulations | |
|---|---|
| Compound of formula (I) | 5.00 |
| C$_{8-13}$ aromatic solvent | 32.00 |
| Cetyl alcohol | 3.00 |
| Polyoxyethylene glycerol monooleate* | 0.75 |
| Polyoxyethylene sorbitan esters* | 0.25 |
| Silicone solution | 0.1 |
| Water | 58.9 |
| | 100.00 |
| 7. Suspension Concentrate | |
| Compound of formula (I) | 10.00 |
| Alkyl aryl ethoxylate* | 3.00 |
| Silicone solution | 0.1 |
| Alkane diol | 5.0 |
| Fumed silica | 0.50 |
| Xanthan gum | 0.20 |
| Water | 80.0 |
| Buffering agent | 1.2 |
| | 100.00 |
| 8. Microemulsion | |
| Compound of formula (I) | 10.00 |
| Polyoxyethylene glycerol monooleate* | 10.00 |
| Alkane diol | 4.00 |
| Water | 76.00 |
| | 100.00 |
| 9. Water Dispersible Granules | |
| Compound of formula (I) | 70.00 |
| Polyvinyl pyrrolidine | 2.50 |
| Alkyl aryl ethoxylate | 1.25 |
| Alkyl aryl sulphonate | 1.25 |
| China clay | 25.00 |
| | 100.00 |
| 10. Granules | |
| Compound of formula (I) | 2.00 |
| Alkyl phenol ethoxylate* | 5.00 |
| Alkyl aryl sulphonate* | 3.00 |
| C$_{8-13}$ aromatic solvent | 20.00 |
| Kieselguhr granules | 70.00 |
| | 100.00 |
| 11. Aerosol (pressure pack) | |
| Compound of formula (I) | 0.3 |
| Piperonyl butoxide | 1.5 |
| C$_{8-13}$ saturated hydrocarbon solvent | 58.2 |
| Butane | 40.0 |
| | 100.00 |
| 12. Aerosol (pressure pack) | |
| Compound of formula (I) | 0.3 |
| C$_{8-13}$ saturated hydrocarbon solvent | 10.0 |
| Sorbitan monooleate* | 1.0 |
| Water | 40.0 |
| Butane | 48.7 |
| | 100.00 |
| 13. Aerosol (pressure pack) | |
| Compound of formula (I) | 1.00 |
| CO$_2$ | 3.00 |
| Polyoxyethylene glycerol monooleate* | 1.40 |
| Propanone | 38.00 |
| Water | 56.60 |
| | 100.00 |
| 14. Lacquer | |
| Compound of formula (I) | 2.50 |
| Resin | 5.00 |
| Antioxidant | 0.50 |
| High aromatic white spirit | 92.0 |
| | 100.00 |
| 15. Spray (ready to use) | |
| Compound of formula (I) | 0.10 |
| Antioxidant | 0.10 |
| Odourless kerosene | 99.8 |
| | 100.00 |
| 16. Potentiated Spray (ready to use) | |
| Compound of formula (I) | 0.10 |
| Piperonyl butoxide | 0.50 |
| Antioxidant | 0.10 |
| Odourless kerosene | 99.30 |
| | 100.00 |
| 17. Microencapsulated | |
| Compound of formula (I) | 10.0 |
| C$_{8-13}$ aromatic solvent | 10.0 |
| Aromatic di-isocyanate# | 4.5 |
| Alkyl phenol ethoxylate* | 6.0 |
| Alkyl diamine# | 1.0 |
| Diethylene triamine | 1.0 |
| Concentrated hydrochloric acid | 2.2 |
| Xanthan gum | 0.2 |
| Fumed silica | 0.5 |
| Water | 64.6 |
| | 100.00 |

\* = Surfactant
\# = react to form the polyurea walls of the microcapsule
Antioxidant could be any of the following individually or combined
Butylated hydroxytoluene
Butylated hydroxyanisole
Vitamin C (ascrobic acid)

BIOLOGICAL DATA

The following examples illustrate, in a non-limiting manner, the pesticidal activity of compounds of formula (I):

EXAMPLE A

Spray Tests

The activity of compounds of the invention were tested by dissolving the compounds in acetone (5%) and then diluting in water: "Synperonic" (94.5%:0.5%) to give a water emulsion. The solution was then used to treat the following insects, for which activity was observed at the following spray rates:

*Musca domestica*

20 female Musca were contained in a cardboard cylinder with gauze over both ends. Solution containing the compound was sprayed onto the insects so enclosed and mortality assessed after 48 hours at 25° C.

The following compounds were active at 1000 ppm or less :
1, 2, 3, 7.

The following compounds were active at 200 ppm or less:
5, 6, 8, 9, 10, 11.

*Pluetella xylostella*

Chinese cabbage leaf discs infested with 8 2nd instar Plutella larvae were sprayed with the solution containing the compound. Mortality was assessed after 2 days at 25° C.

The following compounds were active at 200 ppm or less:
1, 2, 3.

The following compounds were active at 400 ppm or less:
6, 7, 8, 9, 10, 11.

*Tetranychus urticae*

Leaf discs of infested french bean were sprayed with the solution containing the compound. Mortality was assessed after 2 days at 25° C.

The following compounds were active at 1000 ppm or less :
1, 2, 3, 4, 5, 6, 7, 8, 9, 10, 11.

Spodoptera littoralis

Uninfested leaves were sprayed with the test solution containing the compound and left to dry. These were then infested with 10 newly hatched larvae. Mortality was assessed after 3 days.

The following compounds were active at 200 ppm or less:
1, 2, 3, 10.

The following compound was active at 125 ppm or less:
4.

Myzus Dersicae 10 adult Myzus were placed on a leaf disc of chinese cabbage. 24 hours later the disc was sprayed with the solution containing the compound. Mortality was assessed after 2 days at 25° C.

The following compounds were active at 1000 ppm or less:
1, 3, 4, 8, 9, 10.

The following compounds were active at 200 ppm or less:
5, 6, 11.

Diabrotica undecimpunctata

2nd instar larvae and their food were sprayed on filter paper with the solution containing the compound. Activity was assessed at 2 days.

The following compounds were active at 1000 ppm or less:
1, 3

Artificial diet and a filter paper were sprayed with the test solution containing the compound and then infested with 8 2nd instar larvae. Mortality was assessed after 2 days.

The following compounds were active at 1000 ppm or less:
4, 5, 6, 8, 9, 10, 11.

EXAMPLE B

Topical Application tests

Blattella germanica 0.5 μl of a solution of the compound in butanone (with piperonyl butoxide) was topically applied to male *B.germanica*. Mortality was assessed after 6 days.

The following compounds were active at 10 μg or less (with piperonyl butoxide):
1, 2, 4, 5, 8, 9, 11.

We claim:
1. A compound of formula (I):

$$Q-Q^1-CD(R^1)=C(R^2)-C(R^3)=C(R^6)-(=X-)-N(R^5(R^6)$$

or a salt thereof, wherein Q is phenyl, or Q is a dihalovinyl group of a group $R^7-C\equiv C-$ where $R^7$ is $C_{1-4}$ alkyl, tri $C_{1-4}$ alkylsilyl, halogen or hydrogen; $Q^1$ is a 1,2-cyclopropyl ring optionally substituted by 1 to 3 member of the group selected from $C_{1-3}$ alkyl, halo, $C_{1-3}$ haloalkyl, alkynyl or cyano; at least one of $R^1$, $R^2$, $R^3$ and $R^4$ being hydrogen and the others being independently selected from the group consisting of hydrogen, halo, $C_{1-4}$ alkyl and $C_{1-4}$ haloalkyl; $X^1$ is oxygen or sulfur; $R^5$ is $C_{1-8}$ hydrocarbyl optionally substituted by halo, cyano, trifluoromethyl, trifluoromethylthio or $C_{1-6}$ alkoxy; and $R^6$ is selected from the group consisting of (A) $-Y=X^2-(R^8)_a$ where $X^2$ is O or S, Y is carbon, $R^8$ is hydrogen, $C_{1-4}$ alkyl, $C_{1-4}$ alkoxy, $C_{1-5}$ alkylcarbonyl or phenyl or $CO_2R^9$ where $R^9$ is an $C_{1-4}$ alkyl or phenyl, and a is 1 or 2 and
(B) $-CR^{15}R^{16}X^3R^{17}$ wherein $R^{15}$ and $R^{16}$ are hydrogen or $C_{1-4}$ alkyl, $X^3$ is oxygen or sulfur and $R^{17}$ is $C_{1-4}$ alkylcarbonyl or phenyl alkylcarbonyl.

2. A compound of the formula (I) according to claim 1 wherein $R^1$, $R^2$, $R^3$ and $R^4$ are selected from hydrogen, methyl or fluoro.

3. A compound of the formula (I) according to claim 1 wherein the steric configuration of $Q^1$ in the chain is such that the substituents are attached to the ring to give trans geometry.

4. A compound of the formula (I) of claim 1 wherein $R^5$ is selected from the group consisting of $C_{1-4}$ alkyl optionally substituted by $C_{2-7}$ cycloalkyl, and $C_{2-5}$ alkenyl.

5. A compound of the formula (I) of claim 1 wherein $R^6$ is selected from the group consisting of (A) where $X^2$ is oxygen, Y is carbon and $R^8$ is hydrogen, $C_{1-4}$ alkoxy or $CO_2R^9$ where $R^9$ is $C_{1-4}$ alkyl or phenyl, and a is either 1 or 2, (B) where b is 0 and $R^{10}$ is phenyl or a group $N(CH_3)R^{11}$ wherein $R^{11}$ is CHO or $CO_2$alkyl and (C) where $R^{15}$ and $R^{16}$ are hydrogen, $X^3$ is oxygen and $R^{17}$ is $C_{1-4}$ alkyl.

6. An insecticidal or acaricidal composition comprising a compound of formula (I) as defined in claim 1 in admixture with a carrier or diluent.

7. A method for the control of pests comprising applying to the pest or to an environment susceptible to pest infestation an effective amount of a compound of claim 1.

8. A compound of claim 1 which is (±)-(2E,4E)-N-isobutyl-N-phenylthio-5-[trans-2-(3,4-dichlorophenyl)-cyclopropyl]-3-methylpenta-2,4-dienamide.

* * * * *